United States Patent
Israel et al.

(10) Patent No.: US 6,461,381 B2
(45) Date of Patent: *Oct. 8, 2002

(54) FLEXIBLE EXPANDABLE STENT

(75) Inventors: Henry Marshall Israel, Bnei Brak; Gregory Pinchasik, Ramat Hasharon, both of (IL)

(73) Assignee: Medinol, Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/337,629

(22) Filed: Jun. 21, 1999

(65) Prior Publication Data

US 2001/0018595 A1 Aug. 30, 2001

Related U.S. Application Data

(63) Continuation of application No. 09/026,099, filed on Feb. 19, 1998, now Pat. No. 5,972,018, which is a continuation of application No. 08/881,594, filed on Jun. 24, 1997, now Pat. No. 5,843,120, which is a continuation of application No. 08/782,467, filed on Jan. 10, 1997, now abandoned, which is a continuation of application No. 08/457,354, filed on May 31, 1995, now Pat. No. 5,733,303, which is a continuation of application No. 08/282,181, filed on Jul. 28, 1994, now abandoned, and a continuation-in-part of application No. 08/213,272, filed on Mar. 17, 1994, now Pat. No. 5,449,373.

(51) Int. Cl.$^7$ .................................................. A61F 2/06

(52) U.S. Cl. ..................................... 623/1.17; 623/1.15

(58) Field of Search ................................ 606/1, 108, 192, 606/194, 198; 604/96; 623/1, 12, 1.1, 1.15, 1.16, 1.17

(56) References Cited

U.S. PATENT DOCUMENTS

| | | |
|---|---|---|
| 4,733,665 A | 3/1988 | Palmaz |
| 4,739,762 A | 4/1988 | Palmaz .................. 128/343 |
| 4,762,128 A | 8/1988 | Rosenbluth |
| 4,800,882 A | 1/1989 | Gianturco |

(List continued on next page.)

FOREIGN PATENT DOCUMENTS

| | | |
|---|---|---|
| EP | 0 335 341 | 4/1989 |
| EP | 0 540 290 | 5/1993 |
| EP | 0 541 443 | 5/1993 |
| EP | 0 566 807 | 10/1993 |
| EP | 0 606 165 | 7/1994 |
| WO | WO 95/31945 | 11/1995 |
| WO | WO 96/03092 | 2/1996 |

OTHER PUBLICATIONS

Trial Transcript, *Scimed Life Systems, Inc. et al. and Medinol Ltd. v. Johnson & Johnson, et al.*, Civil Action No. 99–904–SLR pp. 1–2246.

Trial Transcript, Civil Action No. 99–904–SLR, pp. 2247–2256 (Reading of Jury Verdict).

Jury Verdict, Civil Action No. 99–904–SLR, pp. 2247–2256.

Docket, Civil Action No. 99–904–SLR.

Defendants' Motion for Leave to File an Amended Answer and Counterclaim, Civil Action No. 99–904–SLR.

(List continued on next page.)

*Primary Examiner*—Michael H. Thaler
(74) *Attorney, Agent, or Firm*—Kenyon & Kenyon

(57) ABSTRACT

There is disclosed a stent for implanting in the body. The stent is formed of a tube having a patterned shape which has first and second meander patterns having axes extending in first and second directions. The first meander patterns can be formed into even and odd first meander patterns. The even and odd first meander patterns are 180° out of phase with each other and the odd patterns occur between every two even patterns. The second meander patterns are intertwined with the first meander patterns. The first and second directions can be orthogonal to each other. The second meander patterns can also be formed of even and odd patterns.

83 Claims, 6 Drawing Sheets

U.S. PATENT DOCUMENTS

| | | |
|---|---|---|
| 4,830,003 A | 5/1989 | Wolff et al. |
| 4,856,516 A | 8/1989 | Hillstead |
| 4,886,062 A | 12/1989 | Wiktor |
| 4,922,905 A | 5/1990 | Strecker |
| 4,950,227 A | 8/1990 | Savin et al. |
| 4,969,458 A | 11/1990 | Wiktor |
| 4,994,071 A | 2/1991 | MacGregor |
| 5,019,085 A | 5/1991 | Hillstead |
| 5,019,090 A | 5/1991 | Pinchuk |
| 5,035,706 A | 7/1991 | Giantureo |
| 5,102,417 A | 4/1992 | Palmaz |
| 5,104,404 A | 4/1992 | Wolff |
| 5,116,365 A | 5/1992 | Hillstead |
| 5,133,732 A | 7/1992 | Wiktor |
| 5,158,548 A | 10/1992 | Lau et al. |
| 5,161,547 A | 11/1992 | Tower |
| 5,195,984 A | 3/1993 | Schatz |
| 5,282,824 A | 2/1994 | Gianturco |
| 5,292,331 A | 3/1994 | Boneau ............... 606/198 |
| 5,314,472 A | 5/1994 | Fontaine |
| 5,330,500 A | 7/1994 | Song |
| 5,354,308 A | 10/1994 | Simon et al. |
| 5,354,309 A | 10/1994 | Schepp et al. |
| 5,383,892 A | 1/1995 | Cardon et al. |
| 5,405,377 A | 4/1995 | Cragg |
| 5,421,955 A | 6/1995 | Lau et al. ............... 216/48 |
| 5,441,515 A | 8/1995 | Khosravi et al. |
| 5,443,496 A | 8/1995 | Schwartz et al. |
| 5,449,373 A | 9/1995 | Pinchasik ............... 606/198 |
| 5,507,767 A | 4/1996 | Maeda et al. |
| 5,514,093 A | 5/1996 | Ellis et al. |
| 5,540,712 A | 7/1996 | Kleshinski et al. |
| 5,554,181 A | 9/1996 | Das |
| 5,593,442 A | 1/1997 | Klein ............... 623/23.64 |
| 5,643,312 A | 7/1997 | Fischell et al. |
| 5,649,952 A | 7/1997 | Lam |
| 5,651,174 A | 7/1997 | Schwartz et al. |
| 5,653,727 A | 8/1997 | Wiktor |
| 5,733,303 A | 3/1998 | Israel et al. ............... 623/1.15 |
| 5,843,120 A | 12/1998 | Israel et al. ............... 623/1.15 |
| 5,879,370 A | 3/1999 | Fischell et al. ............... 606/198 |
| 5,972,018 A | 10/1999 | Israel et al. ............... 606/198 |
| 6,156,052 A * | 12/2000 | Richter et al. ............... 606/191 |
| 6,193,747 B1 | 2/2001 | van Oepen ............... 623/1.15 |

OTHER PUBLICATIONS

Plantiffs' Answering Brief in Opposition to Defendant' Motion for Leave to File an Amended Answer and Counterclaim, Civil Action No. 99–904–SLR.

Appendix to Plantiffs' Answering Brief in Opposition to Defendant' Motion for Leave to File an Amended Answer and Counterclaim, Civil Action No. 99–904–SLR.

Reply Brief in Support of Defendant' Motion for Leave to File an Amended Answer and Counterclaim, Civil Action No. 99–904–SLR.

Order of Aug. 15, 2001, Civil Action No. 99–904–SLR (relating to claim construction).

Memorandum Opinion of Aug. 15, 2001, Civil Action No. 99–904–SLR (decisions on summary judgment motions of non–infringment and validity).

Order of Aug. 15, 2001, Civil Action No. 99–904–SLR (orders regarding decisions on summary judgment motions of non–infringment and validity).

\* cited by examiner

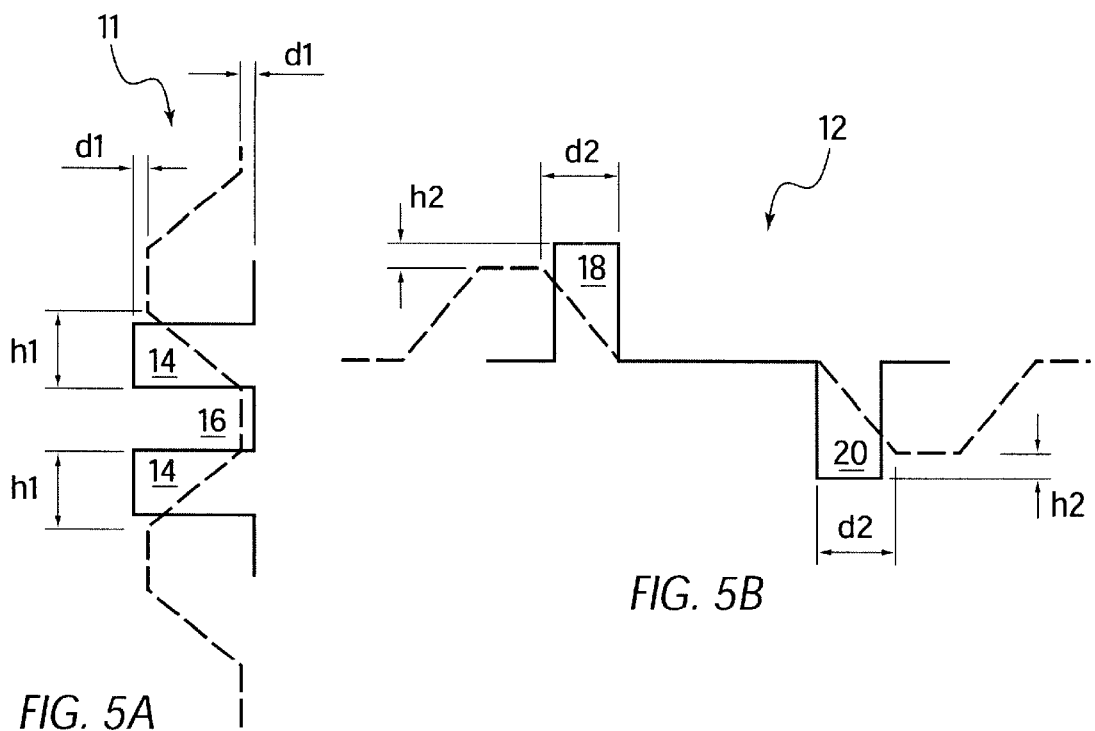
FIG. 5A
FIG. 5B
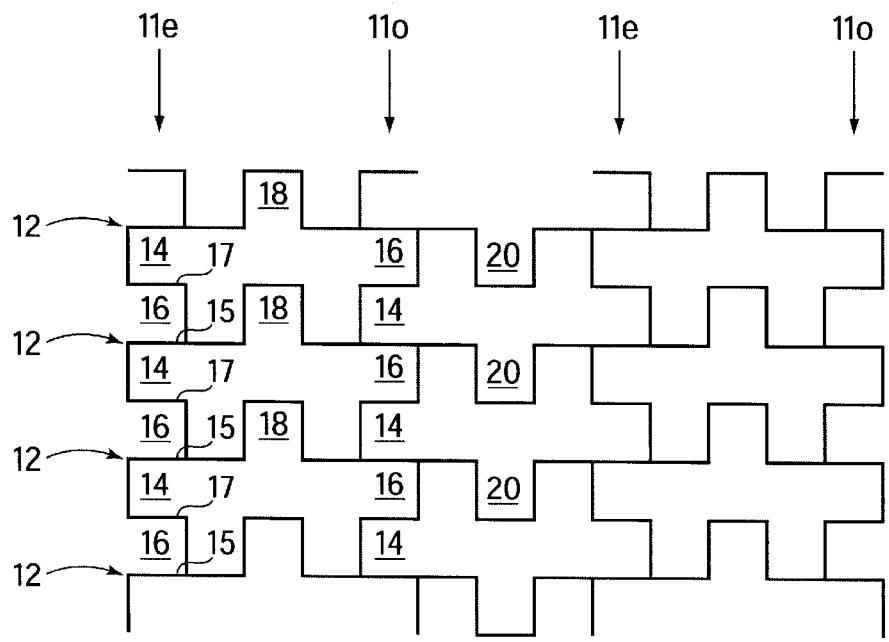
FIG. 6

FLEXIBLE EXPANDABLE STENT

This application is a continuation of Ser. No. 09/026,099, filed Feb. 19, 1998 now U.S. Pat. No. 5,972,018 which is a continuation of Ser. No. 08/881,594, filed Jun. 24, 1997, now U.S. Pat. No. 5,843,120 which application is a continuation of Ser. No. 08/782,467 filed Jan. 10, 1997, now abandoned, which is a continuation of Ser. No. 08/457,354, filed May 31, 1995 (now U.S. Pat. No. 5,733,303), which is a continuation of Ser. No. 08/282,181 filed Jul. 28, 1994 (now abandoned) and a continuation-in-part of Ser. No. 08/213,272, filed Mar. 17, 1994 (now U.S. Pat. No. 5,449,373).

FIELD OF THE INVENTION

The present invention relates generally to stents for implanting into a living body.

BACKGROUND OF THE INVENTION

Various stents are known in the art wherein, for the present application, the term "stent" indicates a device, made of body-compatible material, which is utilized to widen a blood vessel, or other orifice in the body, and to maintain the resultant size of the lumen. Typically, the stent is delivered to the desired location in the body with an inflatable balloon and, when the balloon is inflated, the stent expands, thereby widening the orifice. Other mechanical devices which cause expansion of the stent are also utilized.

Exemplary patents in the field of stents formed of wire are: U.S. Pat. No. 5,019,090 to Pinchuk, U.S. Pat. No. 5,161,547 to Tower, U.S. Pat. No. 4,950,227 to Savin, et al., U.S. Pat. No. 5,314,472 to Fontaine, U.S. Pat. No. 4,886,062 and U.S. Pat. No. 4,969,458 to Wiktor and U.S. Pat. No. 4,856,516 to Hillstead. Stents formed of cut stock metal are described in: U.S. Pat. No. 4,733,665 to Palmaz, U.S. Pat. No. 4,762,128 to Rosenbluth, U.S. Pat. No. 5,102,417 to Palmaz and Schatz, U.S. Pat. No. 5,195,984 to Schatz and WO 91FR013820 to Meadox.

The stents described in U.S. Pat. No. 5,102,417 to Palmaz and Schatz have expandable tubular grafts connected together with a flexible connector. The grafts are formed of a plurality of slots disposed parallel to the longitudinal axis of the tube. The flexible connectors are helical connectors. Since the tubular grafts are relatively rigid, the flexible connectors are needed so that the stents can bend when being fed through a curved blood vessel. When the stents of U.S. Pat. No. 5,102,417 expand, the grafts expand radially and, consequently, shrink longitudinally. However, at the same time, the helical connectors twist. The twisting motion is most probably harmful to the blood vessel.

U.S. Pat. No. 5,195,984 to Schatz describes a similar stent but with one straight connector, paralell to the longitudinal axis of the tubular grafts, between tubular grafts. The straight member removes the twisting motion; however, it is not a very strong connector.

SUMMARY OF THE PRESENT INVENTION

It is therefore an object of the present invention to provide a flexible stent which minimally shrinks, in the longitudinal direction, during expansion.

The stent of the present invention is formed of a tube having a patterned shape which has first and second meander patterns having axes extending in first and second directions wherein the second meander patterns are intertwined with the first meander patterns. The first and second directions can be orthogonal to each other.

In accordance with one embodiment of the present invention, the first meander to patterns are formed into even and odd first meander patterns. The even and odd first meander patterns are 180° out of phase with each other and the odd patterns occur between every two even patterns. The second meander patterns can also be formed of even and odd patterns.

Additionally, in accordance with a preferred embodiment of the present invention, the second meander patterns have two loops per period and the even and odd first meander patterns are connected on first and second sides, respectively, of each loop of the second meander patterns.

Alternatively or in addition, the second meander patterns are formed of even and odd second meander patterns. In this embodiment, the even and odd first meander patterns have loops and the even and odd second meander patterns are connected to the even and odd first meander patterns so as to leave one full loop between each pair of even and odd second meander patterns.

Moreover, in accordance with a preferred embodiment of the present invention, the first and second meander patterns are formed from flat metal. Alternatively, they can be cut from wire. Further, they can be imbedded or covered with any body-compatible material.

BRIEF DESCRIPTION OF THE DRAWINGS

The present invention will be understood and appreciated more fully from the following detailed description taken in conjunction with the drawings in which:

FIGS. 5A and 5B are illustration is of the changes in the patterns of the stent of FIG. 1 due to expansion;

FIG. 6 is a schematic illustration of a second embodiment of the pattern for a stent;

DETAILED DESCRIPTION OF PREFERRED EMBODIMENTS

Figure 1:
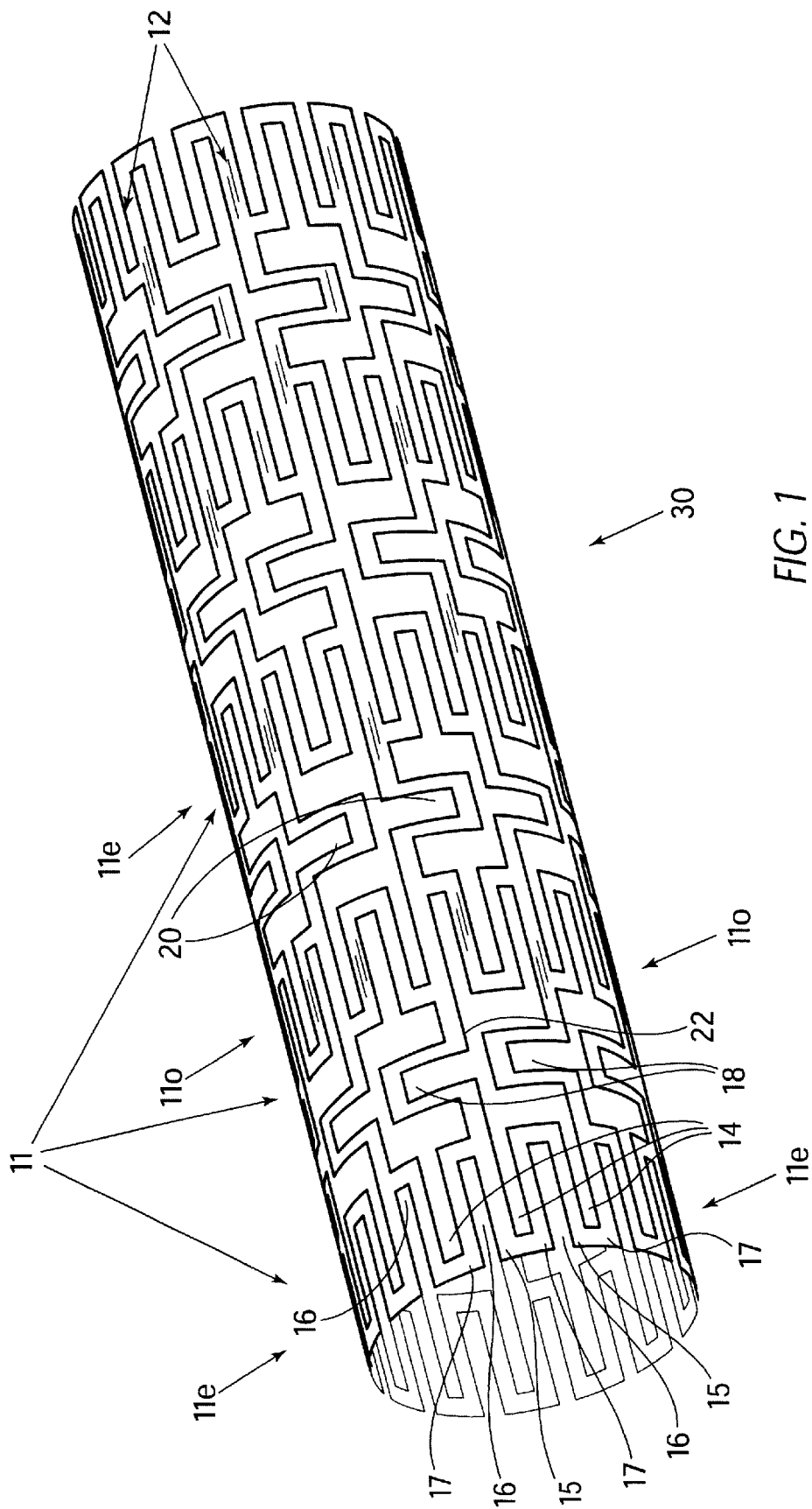
FIG. 1 is an illustration of a patterned stent, constructed and operative in accordance with a first preferred embodiment of the present invention.
Figure 2:
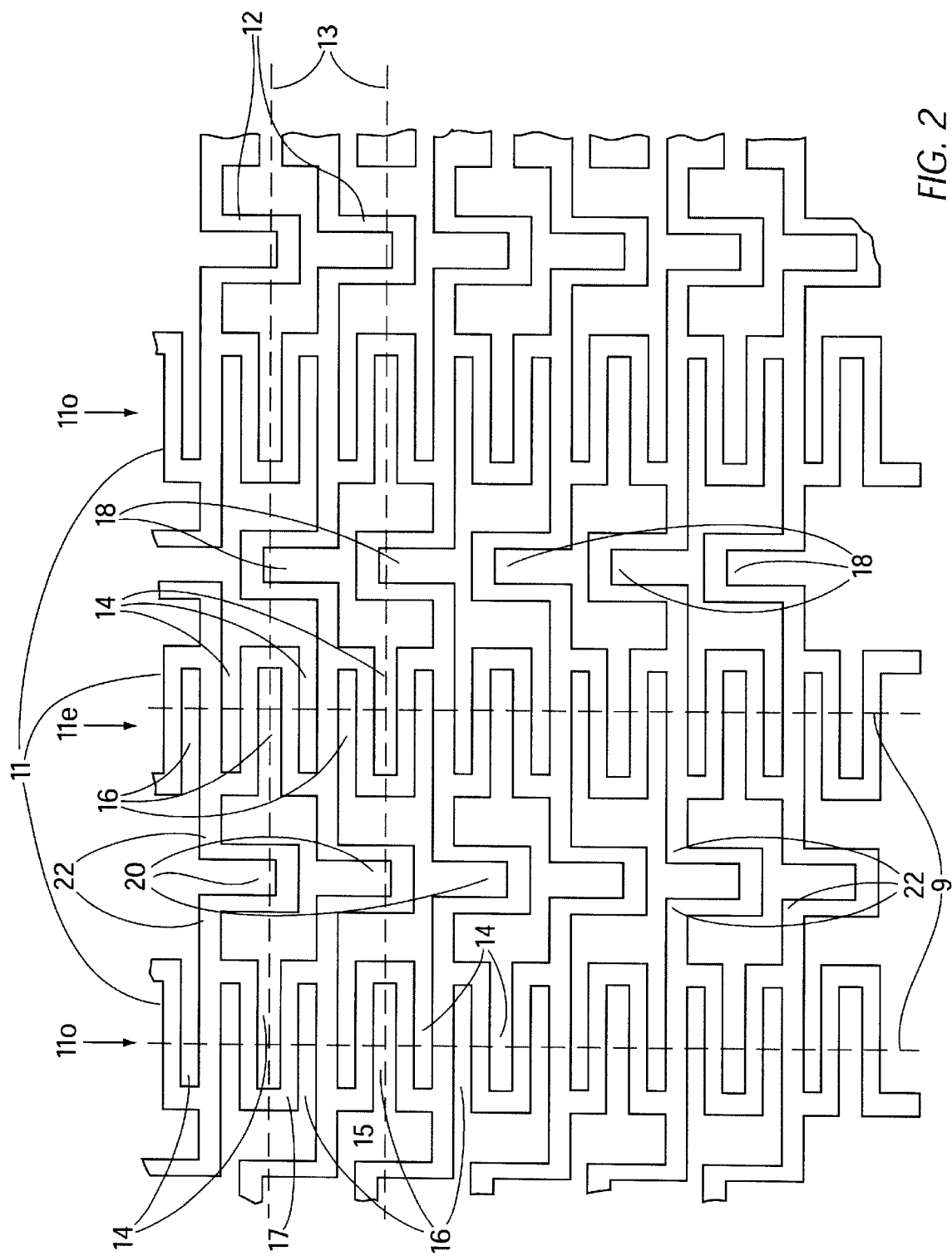
FIG. 2 is an illustration of the pattern of the stent of FIG. 1.
Figure 3:
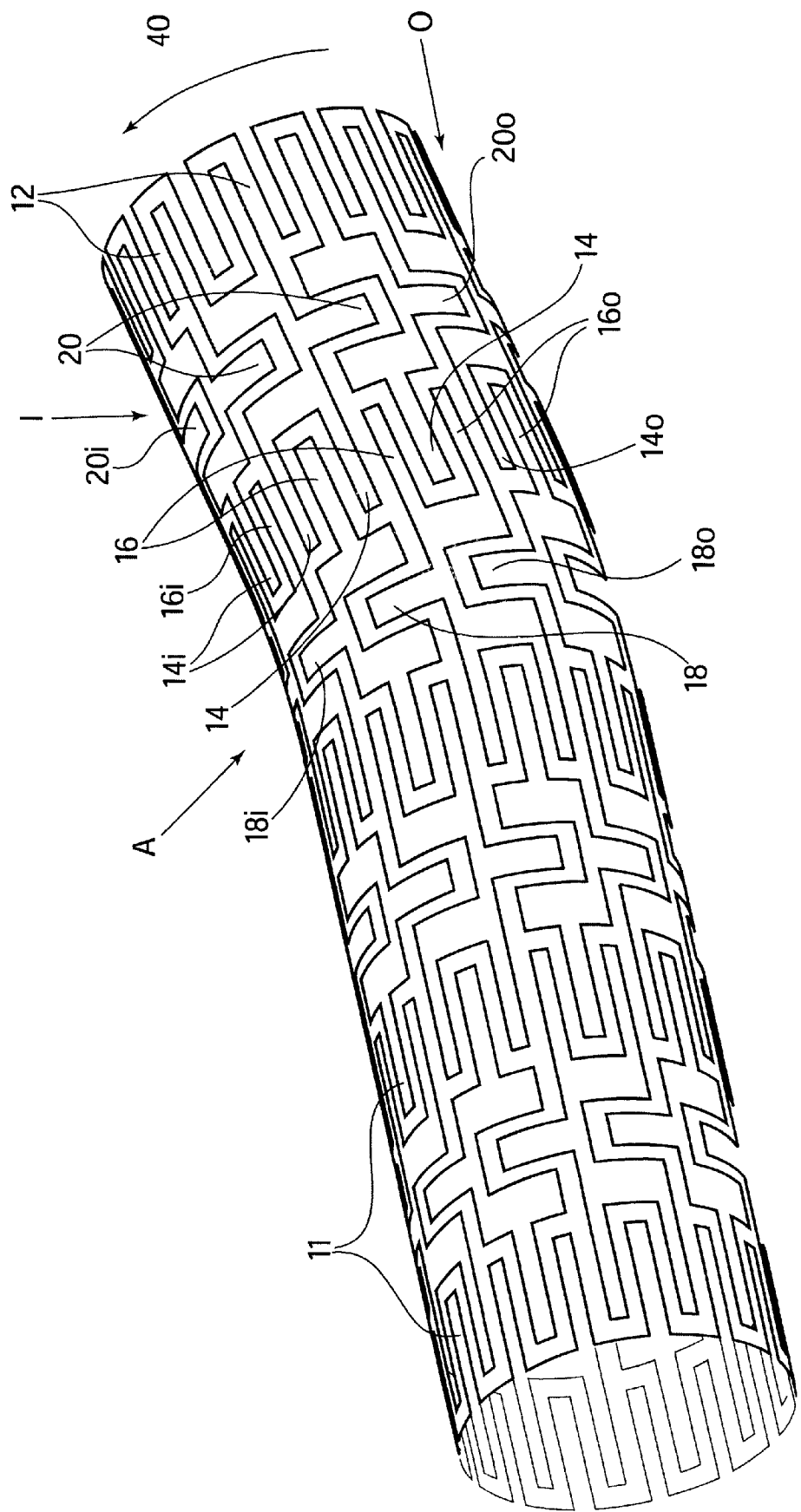
FIG. 3 is an illustration of the stent of FIG. 1 in a bent position.
Figure 4:
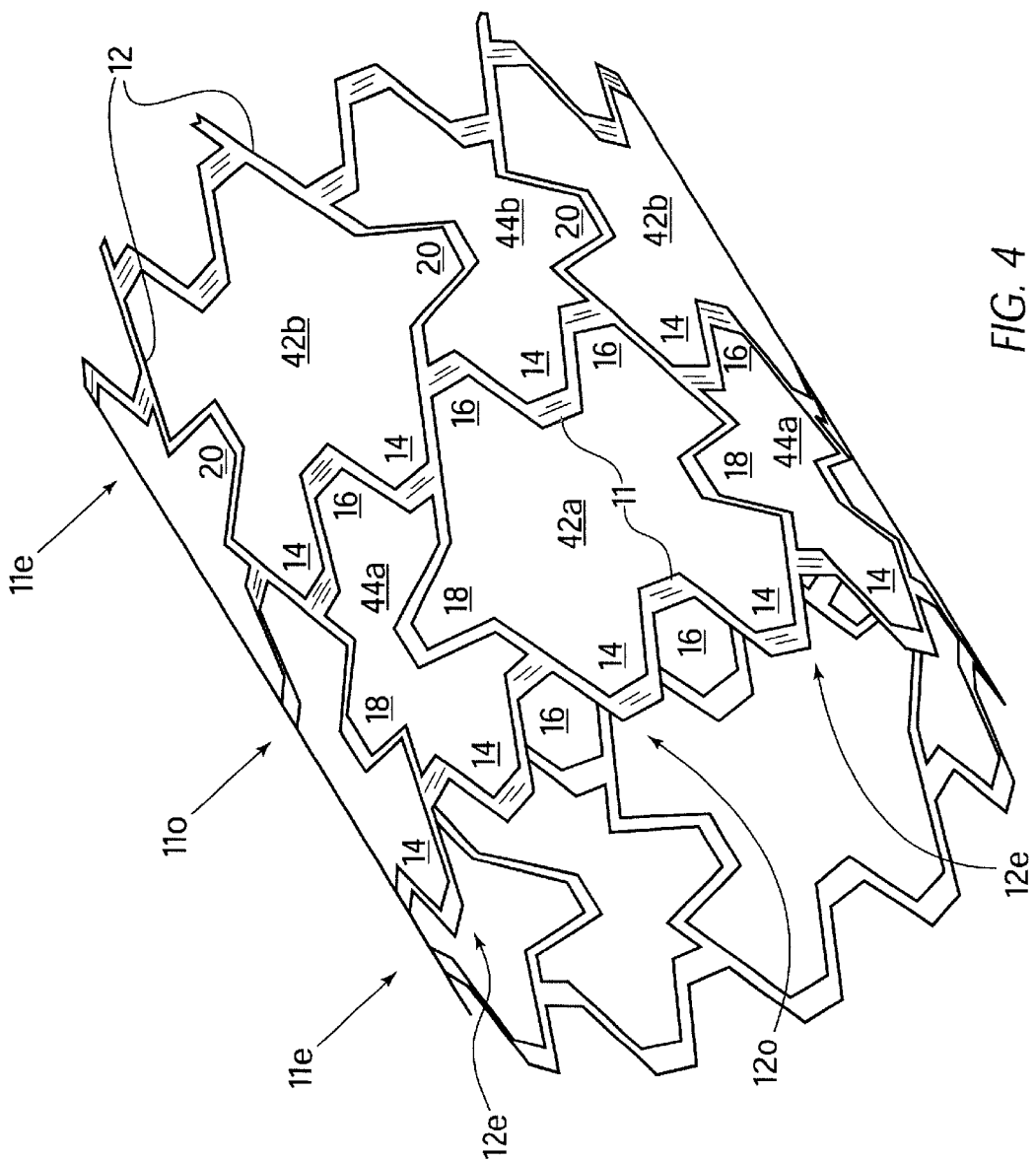
FIG. 4 is an illustration of the stent of FIG. 1 in an expanded format.

Reference is now made, to FIGS. 1–4 which illustrate a first embodiment of a stent, constructed and operative in accordance with the principles of the present invention. FIG. 1 illustrates the stent in its non-expanded form, FIG. 2 illustrates the pattern of the stent, FIG. 3 illustrates it in a partially bent position and FIG. 4 illustrates it in an expanded form. As shown in FIG. 3, the stent 30 defines a longitudinal aperture 80 having a longitudinal axis or longitudinal extension 79.

The stent of the present invention is a tube whose sides are formed into a plurality of each of two orthogonal meander patterns which patterns are intertwined with each other. The term "meander pattern" is taken herein to describe a periodic pattern about a center line and "orthogonal meander patterns" are patterns whose center lines are orthogonal to each other.

In the stent of FIGS. 1–4, the two meander patterns are labeled 11 and 12 and they are most easily seen in FIG. 2. Meander pattern 11 is a vertical sinusoid having a vertical center line 9. Meander pattern 11 has two loops 14 and 16 per period wherein loops 14 open to the right while loops 16 open to the left. Loops 14 and 16 share common members 15 and 17, where (member 15)connects from one loop 14 to its following loop 16 and member 17 connects from one loop 16 to its following loop 14.

Meander pattern 12 is an horizontal pattern having an horizontal center line 13. Meander pattern 12 also has loops labeled 18 and 20, but between loops of a period is an extended straight section labeled 22. Loops 18 open downwards and loops 20 open upwards.

Vertical meander pattern 11 is provided in odd and even (o and e) versions which are 180° out of phase with each other. Thus, each left opening loop 16 of meander pattern 11o faces a right opening loop 14 of meander pattern 11e and a right opening loop 14 of meander pattern 11o faces a left opening loop 16 of meander pattern 11e.

Horizontal meander pattern 12 is also provided in odd and even forms. The straight sections 22 of horizontal meander pattern 12e intersect with every third common member 17 of vertical meander pattern 11e. The straight sections 22 of horizontal meander pattern 12o intersect with every third common member 15 of vertical meander pattern 11e, beginning with the common member 15 two after an intersected common member 17. The result is a full loop 14 between meander patterns 12e and 12o and a full loop 16 between meander patterns 12o and 12e.

Returning to FIG. 1, the pattern of FIG. 2 is formed into a tube 30 of an easily deformable material, such as a metal. Due to the two meander patterns, the stent of FIG. 1, when attached over a catheter balloon, is flexible and can therefore be easily dragged through curved blood vessels. An example of the way in which the stent of FIG. 1 bends is illustrated in FIG. 3.

In FIG. 3, the stent begins to bend at the point marked A in the direction marked by arrow 40. As the stent begins to curve, the section marked I becomes the inside of the curve while the section marked O becomes the outside of the curve. The inside of the curve I is shortened vis-a-vis the outside of the curve O.

During bending, the loops 14–20 to the right of the point A change shape in order to compensate for the differences in length between the inside and outside curves. For to example, loops 18i and 20i near the inside of the curve are closer together than loops 18o and 20o on the outside of the curve, which expand. Loops 14i and 16i near the inside I are compressed while the loops 14o and 16o closer to the outside O of the curve are expanded.

As can be seen, both meander patterns 11 and 12 are involved in the bending Although not shown, it will be appreciated that the stent of FIGS. 1–4 can bend in any direction and in more than one direction at any time.

FIG. 4 illustrates the stent of FIG. 1 in its expanded form. When the stent expands, both meander patterns 11 and 12 expand (i.e. all loops 14–20 open up). As can be seen, the expanded stent has two types of enclosed spaces, a large space 42 between meander patterns 12o and 12e and a small space 44 between meander patterns 12e and 12o. As can also be seen, each large space 42 has two loops 14 on its left side and two loops 16 on its right side. The large spaces between vertical meander patterns 11e and 11o, which are labeled 42a, have loops 18 at their tops and bottoms while the large spaces between vertical meander patterns 11o and 11e, which are labeled 42b, have loops 20 at their tops and bottoms. Similarly for small spaces 44a and 44b.

It is noted that, due to the orthogonal meander patterns 11 and 12, the stent of FIG. 1 does not significantly shrink during expansion. This is illustrated in detail in FIGS. 5A and 5B to which reference is now made. FIG. 5A illustrates the movement, during expansion, of one vertical meander pattern 11 and FIG. 5B illustrates the movement, during expansion, of one horizontal meander pattern 12. The original patterns are shown with solid lines and the expanded patterns are shown pith dashed lines.

The vertical meander pattern 11 of FIG. 5A expands by widening its loops 14 and 16. As a result, the vertical meander pattern 11 grows vertically by an amount $2*h_1$ per loop. However, it also shrinks horizontally, by an amount $2*d_1$. Similarly, the horizontal meander pattern 12 of FIG. 5B expands by widening its loops 18 and 20. As a result, the horizontal meander pattern 12 growths horizontally by an amount $2*d_2$ per loop. However, it also shrinks vertically, by an amount $h_2$. Thus, the vertical growth of the vertical meander pattern 11 compensates, at least partially, for the vertical shrinkage of the horizontal meander pattern 12, and vice versa. It is noted that the end portions of any stent are only partially compensated and therefore, may shrink somewhat.

It will be appreciated that the two orthogonal meander patterns 11 and 12 and the compensation they provide to each other provides flexibility to the unexpanded stent of FIG. 1. However, when the stent is expanded, the changes in each of loops 14 and 16 provide rigidity to the resultant stent and thus, enable the stent to maintain a blood vessel at a desired inner diameter.

The stent of the present invention can be manufactured from flat metal which is etched into the pattern of FIG. 2. The etched metal is then bent to form the tube 30. Alternatively, the pattern of FIG. 2 can be manufactured from welded or twisted wire.

It will be appreciated that the stent of the present invention can be made from metal and/or wire. Additionally, it can be plated with a protective material, embedded with a medicine, and/or covered with a material which can fill in the spaces 42 and 44.

Figure 7:
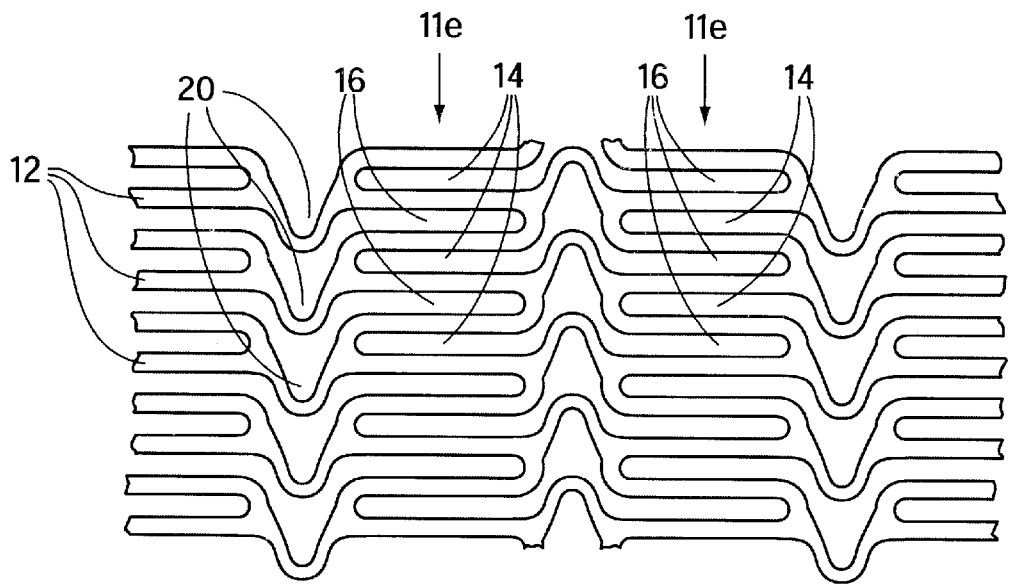
FIG. 7 is an illustration of a third embodiment of the pattern for the stent.
Figure 8:
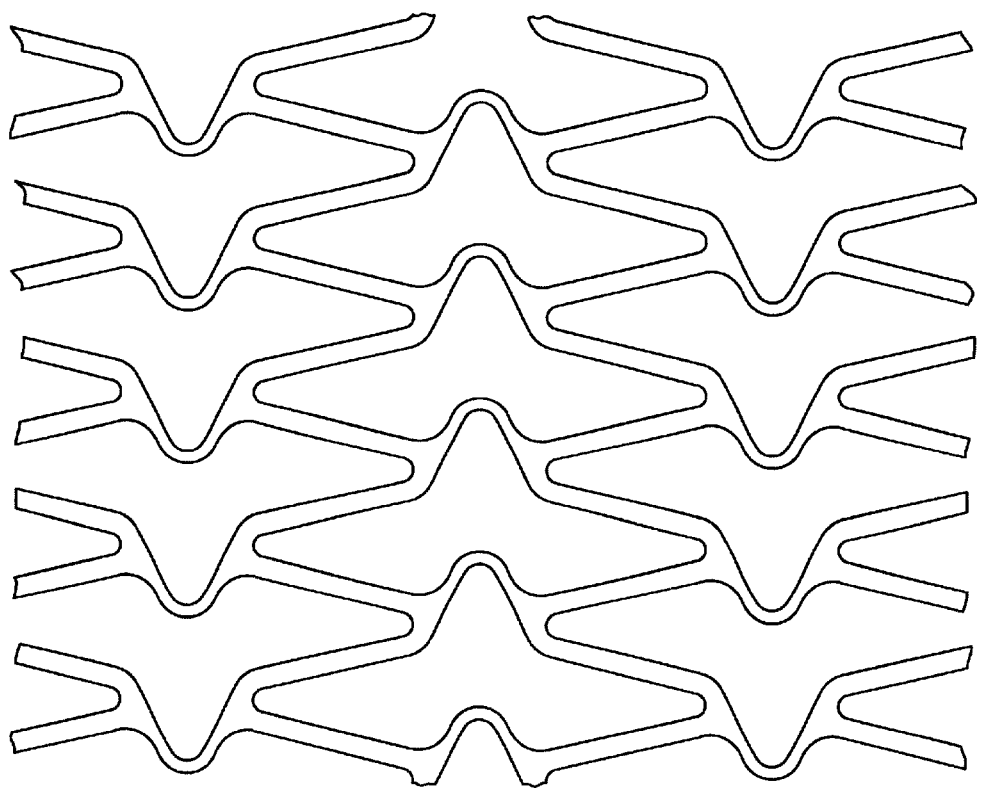
FIG. 8 is an illustration of the pattern of FIG. 7 in an expanded format.

It will be appreciated that the present invention encompasses all stents manufactured with a pattern formed of two meander patterns, orthogonal or otherwise. Another exemplary pattern, also faith orthogonal meander patterns, is provided herein wherein FIG. 6 is a schematic version and FIG. 7 is a more rounded version. FIG. 8 shows the pattern of FIG. 7 in an expanded format. The pattern of FIGS. 6 and 7 is similar to that shown in FIG. 2 except that it has more horizontal meander patterns 12 and they are of one kind, rather than being even and odd as in FIG. 2.

As can be seen in both FIGS. 6 and 7, there are two types of vertical meander patterns 11e and 11o which are 180° out of phase with each other. The horizontal meander patterns 12 connect with every line 15 of vertical meander pattern 11e.

FIG. 8 illustrates the pattern of FIG. 7 in an expanded format. Since there are no even and odd horizontal meander patterns, in the expanded format of FIG. 8, there are no large and small spaces. Instead, all spaces are of the same size, i.e., the stent is comprised of a plurality of spaces or cells 50 defining a uniform cellular structure.

As shown in FIGS. 3, 7 and 8, Applicants' invention can also be described as an expandable stent defining a longitudinal aperture 80 having a longitudinal axis or extension 79 and a circumferential axis or extension 105, including a plurality of flexible connected cells 50 with each of the flexible cells 50 having a first longitudinal end 77 and a second longitudinal end 78. Each cell 50 also is provided with a first longitudinal apex 100 disposed at the first longitudinal end 77 and a second longitudinal apex 104 disposed at the second longitudinal end 78. Each cell 50 also includes a first member 51 having a longitudinal component having a first end 52 and a second end 53; a second member 54 having a longitudinal component having a first end 55 and a second end 56; a third member 57 having a longitudinal component having a first end 58 and a second end 59; and a fourth member 60 having a longitudinal component having a first end 61 and a second end 62. The stent also includes a first loop 63 defining a first angle 64 disposed between the first end 52 of the first member 51 and the first end 55 of the second member 54. A second loop 65 defining a second angle 66 is disposed between the second end 59 of the third member 57 and the second end 62 of the fourth member 60 and is disposed generally opposite to the first loop 63. A first flexible compensating member or flexible link 67 having a first end 68 and a second end 69 is disposed between the first member 51 and the third member 57 with the first end 68 of the first flexible compensating member or flexible link 67 communicating with the second end 53 of the first member 51 and the second end 69 of the first flexible compensating member or flexible link 67 communicating with the first end 58 of the third member 57. The first end 68 and the second end 69 are disposed a variable longitudinal distance 70 from each other. A second flexible compensating member 71 having a first end 72 and a second end 73 is disposed between the second member 54 and the fourth member 60. The first end 72 of the second flexible compensating member or flexible link 71 communicates with the second end 56 of the second member 54 and the second end 73 of the second flexible compensating member or flexible link 71 communicates with the first end 61 of the fourth member 60. The first end 72 and the second end 73 are disposed a variable longitudinal distance 74 from each other. In a preferred embodiment, the first and second flexible compensating member or flexible links 67 and 71 are arcuate. The first and second flexible compensating member or flexible links 67 and 71 are differentially extendable or compressible when the stent is bent in a curved direction away from the longitudinal axis 79 of the aperture 80. (Shown in FIG. 3.) The first member 51, second member 54, third member 57, and fourth member 60 and the first loop 63 and the second loop 65 and the first flexible compensating member or flexible link 67 and the second flexible compensating member or flexible link 71 are disposed so that as the stent is expanded the distance between the first flexible compensating member or flexible link 67 and the second flexible compensating member or flexible link 71 increases and the longitudinal component of the first member 51, second member 54, third member 57 and fourth member 60 decreases while the first loop 63 and the second loop 65 remain generally opposite to one another, the ends 68 and 69 of the first flexible compensating member or flexible link 67 and the ends 72 and 73 of the second flexible compensating member or flexible link 71 open so as to increase the variable longitudinal distance 70 between the first end 68 and the second end 69 of the first flexible compensating member or flexible link 67 and so as to increase the variable longitudinal distance 74 between the first end 72 and the second end 73 of the second flexible compensating member or flexible link 71. This compensates for the decreasing of the longitudinal component of the first member 51, second member 54, third member 57, and fourth member 60 and substantially lessens the foreshortening of the stent upon its expansion. In a preferred embodiment, and as shown in FIG. 5A, the flexible compensating member or flexible links 67 and 71 compensate in an amount that is substantially equal to the amount that the stent foreshortens. As shown in FIGS. 7 and 8, the first flexible compensating member or flexible link 67 and the second flexible compensating member or flexible link 71 in each cell 50 of each row or band of cells 101, 102 and 103, serve to flexibly connect other cells 50 in adjacent rows or bands 102, 103, and 104 which themselves have first and second compensating members 67 and 71. As shown in FIG. 7, the first flexible compensating member or flexible links 67 and 71 in row or band 101 serve to flexibly connect the cells 50 in adjacent rows or bands 102 and 103. As shown in FIGS. 7 and 8, a portion of the flexible member 67 or 71 disposed between the first ends 68 and 72 and the second ends 69 and 73 may be provided with a width that is smaller than the width of the apices 100 and 104 to which they are attached.

It will be appreciated, by persons skilled in the art that the present invention is not limited to what has been particularly shown and described hereinabove.

Rather the scope of the present invention is defined by the claims which follow:

1. A stent for implanting in the body and expanding to hold open a blood vessel, which stent both before and after its intended expansion, comprises:

a) a body-compatible metal mesh defining a tube having a plurality of longitudinally adjacent contiguous cells, each of the cells comprising one pair of longitudinally facing loops, each longitudinally facing loop having a generally curved apex and having portions with a substantial longitudinal component extending from said apex, said portions forming walls of the cells, wherein at least some of said portions are also walls of longitudinally adjacent cells, the pair of longitudinally facing loops generally opposite to and facing one another, each of the facing loops adapted to open further upon radial expansion of the stent which tends to foreshorten the stent longitudinally, and b) each of the cells further comprising a pair of members that include flexible curved portions, which members are disposed between the adjacent pair of facing loops and integral therewith to complete each of the cells, the pair of members made of a metal such that, upon curvature of the stent, the members will bend to facilitate flexing of the stent along the longitudinal axis and will, upon expansion of the stent, bend to substantially offset foreshortening along the longitudinal axis.

2. The stent of claim 1 wherein:

(a) said plurality of cells includes all cells in said stent except for the cells disposed at the ends of the stent, and each wall of each of the plurality of cells also comprises the wall of an adjacent cell and, (b) each facing loop of each of the plurality of cells is connected to a facing loop in another cell by one of said members.

3. The stent of claim 2 wherein one pair of facing loops is disposed between each pair of members.

4. The stent of claim 3 wherein the curved apices of a pair of facing loops are generally aligned along the longitudinal axis of the stent.

5. The stent of claim 4 wherein the flexible curved portions are u-shaped.

6. The stent of claim 3 wherein the flexible curved portions are u-shaped.

7. The stent of claim 1 wherein the stent is adapted to be positioned on a balloon which upon expansion causes the stent to expand to hold open the blood vessel.

8. The stent of claim 7 wherein the mesh is comprised of a metal which is balloon expandable.

9. The stent of claim 8, wherein the stent is provided with a coating.

10. The stent of claim 7 wherein one pair of facing loops is disposed between each pair of members.

11. The stent of claim 10 wherein the curved apices of a pair of facing loops are generally aligned along the longitudinal axis of the stent.

12. The stent of claim 11 wherein the flexible curved portions are u-shaped.

13. The stent of claim 10 wherein the flexible curved portions are u-shaped.

14. The stent of claim 7 wherein the curved apices of a pair of facing loops are generally aligned along the longitudinal axis of the stent.

15. The stent of claim 14 wherein the flexible curved portions are u-shaped.

16. The stent of claim 7 wherein the flexible curved portions are u-shaped.

17. The stent of claim 1, in which the expanded stent has approximately the same longitudinal length as the stent had prior to expansion.

18. The stent of claim 17 wherein one pair of facing loops is disposed between each pair of members.

19. The stent of claim 18 wherein the curved apices of a pair of facing loops are generally aligned along the longitudinal axis of the stent.

20. The stent of claim 19 wherein the flexible curved portions are u-shaped.

21. The stent of claim 18 wherein the flexible curved portions are u-shaped.

22. The stent of claim 17 wherein the curved apices of a pair of facing loops are generally aligned along the longitudinal axis of the stent.

23. The stent of claim 22 wherein the flexible curved portions are u-shaped.

24. The stent of claim 17 wherein the flexible curved portions are u-shaped.

25. The stent of claim 1 wherein the mesh is comprised of a metal which is balloon expandable.

26. The stent of claim 25, wherein the stent is provided with a coating.

27. The stent of claim 1 wherein one pair of facing loops is disposed between each pair of members.

28. The stent of claim 27 wherein the curved apices of a pair of facing loops are generally aligned along the longitudinal axis of the stent.

29. The stent of claim 28 wherein the flexible curved portions are u-shaped.

30. The stent of claim 27 wherein the flexible curved portions are u-shaped.

31. The stent of claim 1 wherein the curved apices of a pair of facing loops are generally aligned along the longitudinal axis of the stent.

32. The stent of claim 31 wherein the flexible curved portions are u-shaped.

33. The stent of claim 1 wherein the flexible curved portions are u-shaped.

34. The stent of claim 2 wherein the stent is adapted to be positioned on a balloon which upon expansion causes the stent to expand to hold open the blood vessel.

35. The stent of claim 2, in which the expanded stent has approximately the same longitudinal length as the stent had prior to expansion.

36. The stent of claim 2 wherein the mesh is comprised of a metal which is balloon expandable.

37. The stent of claim 2 wherein the flexible curved portions are u-shaped.

38. The stent of claim 2 wherein the curved apices of a pair of facing loops are generally aligned along the longitudinal axis of the stent.

39. A balloon expandable stent suitable for implantation into a lumen for expansion to support the lumen, said stent made of a unitary piece of metal and said stent in both the unexpanded and in the balloon-expanded state including:
 a plurality of flexible cells adjacent to one another both circumferentially and longitudinally, each of said flexible cells comprising:
  a) a first member having a first end and a second end;
  b) a second member having a first end and a second end;
  c) a third member having a first end and a second end;
  d) a fourth member having a first end and a second end;
  e) a first loop defining a first angle disposed between said first end of said first member and said first end of said second member;
  f) a second loop defining a second angle disposed between said second end of said third member and said second end of said fourth member;
  g) a first flexible link, including an arc, said first flexible link disposed between said second end of said first member and said first end of said third member; and
  h) a second flexible link, including an arc, said second flexible link disposed between said second end of said second member and said first end of said fourth member,
 wherein each of at least two members of said first, second, third and fourth members in each of said cells is also a first, second, third or fourth member of a longitudinally adjacent flexible cell, and
 wherein in the expanded state the first, second, third, and fourth members have a substantial longitudinal component to provide coverage of the lumen.

40. A stent according to claim 39, wherein in the unexpanded state a radial plane perpendicular to a longitudinal axis of the stent can pass through the flexible links of the flexible cells and not pass through any of said first, second, third, or fourth members.

41. A stent according to claim 40, wherein the first and second loops are aligned with respect to each other along the longitudinal axis of the stent.

42. A stent according to claim 40, wherein the stent is provided with a coating.

43. A stent according to claim 40 with at least five cells circumferentially adjacent to each other.

44. A stent according to claim 40, wherein the first members of circumferentially adjacent cells are connected in a closed circumferential structure which contains at least five loops and the second members of circumferentially adjacent cells are connected in a closed circumferential structure which contains at least five loops.

45. A stent according to claim 40 where in each of said first and second flexible links has ends generally aligned with respect to each other along a longitudinal axis of the stent.

46. A stent according to claim 40 wherein said plurality of flexible cells provide substantially all the support for said stent.

47. A stent according to claim 39 with at least five cells circumferentially adjacent to each other.

48. A stent according to claim 47, wherein the stent is provided with a coating.

49. A stent according to claim 39, wherein the first members of circumferentially adjacent cells are connected in a closed circumferential structure which contains at least five loops and the second members of circumferentially adjacent cells are connected in a closed circumferential structure which contains at least five loops.

50. A stent according to claim 49, wherein the stent is provided with a coating.

51. A stent according to claim 39 wherein each of said first and second flexible links has ends generally aligned with respect to each other along a longitudinal axis of the stent.

52. A stent according to claim 39 wherein said plurality of flexible cells provide substantially all the support for said stent.

53. A stent according to claim 39, wherein the stent is provided with a coating.

54. A balloon expandable stent suitable for implantation into a lumen for expansion to support the lumen, said stent made of a unitary piece of metal and said stent in both the unexpanded and in the balloon-expanded state including:
   a plurality of flexible cells adjacent to one another both circumferentially and longitudinally, each of said flexible cells comprising:
      a) a first member having a first end and a second end;
      b) a second member having a first end and a second end,
      c) a third member having a first end and a second end;
      d) a fourth member having a first end and a second end,
      e) a first loop defining a first angle disposed between said first end of said first member and said first end of said second member;
      f) a second loop defining a second angle disposed between said second end of said third member and said second end of said fourth member;
      g) a first flexible link including an arc, said first flexible link disposed between said second end of said first member and said first end of said third member; and
      h) a second flexible link including an arc, said second flexible link disposed between said second end of said second member and said first end of said fourth member,
   wherein each of at least two members of said first, second, third and fourth members in each of said cells is also a first, second, third or fourth member of a longitudinally adjacent flexible cell, and
   wherein said plurality of connected cells imparts radial strength to said stent and provides coverage of the surface of said lumen in an amount sufficient to support said lumen after said stent is expanded by a balloon from a delivery diameter to a deployment diameter.

55. A stent according to claim 54, wherein in the unexpanded state a radial plane perpendicular to a longitudinal axis of the stent can pass through the flexible links of the flexible cells and not pass through any of said first, second, third, or fourth members.

56. A balloon expandable stent for implantation into a lumen to support the lumen, said stent both in the unexpanded state and in the balloon-expanded state including:
   a plurality of flexible cells adjacent to one another both circumferentially and longitudinally each of said flexible cells comprising:
      a) a first flexible link including an arc, the first flexible link having a first longitudinal end and a second longitudinal end;
      b) a second flexible link including an arc, the second flexible link having a first longitudinal end and a second longitudinal end;
      c) a first circumferential member disposed between said first longitudinal end of said first flexible link and said first longitudinal end of said second flexible link and;
      d) a second circumferential member disposed between said second longitudinal end of said first flexible link and said second longitudinal end of said second flexible link,
      e) at least one of said first circumferential member and said second circumferential member in each of said cells having a portion with a substantial longitudinal component that is also a portion with a substantial longitudinal component of a first circumferential member or a second circumferential member in a longitudinally adjacent cell,
   wherein in the expanded state the first and second circumferential members have a substantial longitudinal component to provide coverage of the lumen.

57. A stent according to claim 56, wherein in the unexpanded state, a radial plane perpendicular to a longitudinal axis can pass through the flexible links of the flexible cells and not pass through the circumferential members.

58. A stent according to claim 56 wherein each of said first and second flexible links has ends generally aligned with respect to each other along a longitudinal axis of the stent.

59. A stent according to claim 56 with at least five cells circumferentially adjacent to each other.

60. A stent according to claim 59 wherein the, stent is provided with a coating.

61. A stent according to claim 56, wherein the first members of circumferentially adjacent cells are connected in a closed circumferential structure which contains at least five loops and the second members of circumferentially adjacent cells are connected in a closed circumferential structure which contains at least five loops.

62. A stent according to claim 61 wherein the stent is provided with a coating.

63. A stent according to claim 56 wherein said plurality of flexible cells provide substantially all the support for said stent.

64. A stent according to claim 56, wherein the stent is provided with a coating.

65. A balloon expandable stent for implantation into a lumen to support the lumen, said stent both in the unexpanded state and in the balloon-expanded state including:
   a plurality of flexible cells adjacent to one another both circumferentially and longitudinally each of said flexible adjacent cells comprising:
      a) a first flexible link including an arc, the first flexible link having a first longitudinal end and a second longitudinal end;
      b) a second flexible link including an arc, the second flexible link having a first longitudinal end and a second longitudinal end;
      c) a first circumferential member disposed between said first longitudinal end of said first flexible link and said first longitudinal end of said second flexible link and;
      d) a second circumferential member disposed between said second longitudinal end of said first flexible link and said second longitudinal end of said second flexible link,
      e) at least one of said first circumferential member and said second circumferential member in each of said cells having a portion with a substantial longitudinal component that is also a portion with a substantial longitudinal component of a first circumferential member or a second circumferential member in a longitudinally adjacent cell, f) wherein said plurality of connected flexible cells imparts radial strength to said stent and coverage of the surface of said lumen in an amount sufficient to support said lumen when said stent is expanded by a balloon from a delivery diameter to a deployment diameter.

66. A stent according to claim 65, wherein in the unexpanded state, a radial plane perpendicular to a longitudinal axis can pass through the flexible links of the flexible cells and not pass through the circumferential members.

67. A stent according to claim 65 with at least five cells circumferentially adjacent to each other.

68. A stent according to claim 65, wherein the first members of circumferentially adjacent cells are connected in a closed circumferential structure which contains at least five loops and the second members of circumferentially adjacent cells are connected in a closed circumferential structure which contains at least five loops.

69. A stent according to claim 65 wherein each of said first and second flexible links has ends generally aligned with respect to each other along a longitudinal axis of the stent.

70. A stent according to claim 65 wherein said plurality of flexible cells provide substantially all the support for said stent.

71. A stent according to claim 65, wherein the stent is provided with a coating.

72. A balloon expandable stent suitable for implantation into a lumen to support the lumen, wherein both in the unexpanded state and in the balloon-expanded state, the stent comprises a plurality of flexible cells adjacent to one another both circumferentially and longitudinally each of said flexible cells comprising:
  a) a first member having a first end and a second end;
  b) a second member having a first end and a second end,
  c) a third member having a first end and a second end;
  d) a fourth member having a first end and a second end;
  e) a first loop defining a first angle disposed between said first end of said first member and said first end of said second member;
  f) a second loop defining a second angle disposed between said second end of said third member and said second end of said fourth member;
  g) a first flexible link, including an arc, said first flexible link disposed between said first member and said third member; and
  h) a second flexible link, including an arc, said second flexible link disposed between said second member and said fourth member, wherein each of at least two members of said first, second, third and fourth members in each of said cells is also a first, second, third or fourth member of a longitudinally adjacent flexible cell, and wherein in the expanded state each of the first, second, third, and fourth members has a substantial longitudinal component to provide coverage of the lumen.

73. A stent according to claim 72, wherein in the unexpanded state, a radial plane perpendicular to a longitudinal axis can pass through the flexible links of the flexible cells and not pass through the circumferential members.

74. A stent according to claim 73, wherein at least five first loops and five second loops are located around the circumference of the stent.

75. A stent according to claim 73, wherein the first flexible link is attached at the second end of the first member and the first end of the third member.

76. A stent according to claim 73, wherein the second flexible link is attached at the second end of the second member and the first end of the fourth member.

77. A stent according to claim 72, wherein at least five first loops and five second loops are located around the circumference of the stent.

78. A stent according to claim 72, wherein the first flexible link is attached at the second end of the first member and the first end of the third member.

79. A stent according to claim 72, wherein the second flexible link is attached at the second end of the second member and the first end of the fourth member.

80. A stent according to claim 72 with at least five cells circumferentially adjacent to each other.

81. A stent according to claim 72 wherein each of said first and second flexible links has ends generally aligned with respect to each other along a longitudinal axis of the stent.

82. A stent according to claim 72 wherein said plurality of flexible cells provides substantially all the support for said stent.

83. A stent according to claim 72 wherein the stent is provided with a coating.

* * * * *

UNITED STATES PATENT AND TRADEMARK OFFICE
CERTIFICATE OF CORRECTION

PATENT NO.    : 6,461,381 B2
DATED         : October 8, 2002
INVENTOR(S)   : Israel et al.

It is certified that error appears in the above-identified patent and that said Letters Patent is hereby corrected as shown below:

Column 1,
Lines 1-13, change "This application is a continuation of Ser. No. 09/026,099, filed Feb. 19, 1998 now U.S. Pat. No. 5,972,018 which is a continuation of Ser. No. 08/881,594 filed Jun. 24,1997, now U.S. Pat. No. 5,843,120 which application is a continuation of Ser. No. 08/782,467 filed Jan. 10, 1997, now abandoned, which is a continuation of Ser. No. 08/457,354, filed May 31, 1995 (now U.S. Pat. No. 5,733,303); which is a continuation of Ser. No. 08/282,181 filed Jul. 28, 1994 (now abandoned) and a continuation-in-part of Ser. No. 08/213,272, filed Mar. 17, 1994 (now U.S. Pat. No. 5,449,373)." to -- This application is a continuation of application Serial No. 09/026,099 filed February 19, 1998 (now U.S. Patent No. 5,972,018 issued October 26, 1999), which is a continuation of application Serial No. 08/881,594 filed June 24, 1997 (now U.S. Patent No. 5,843,120, issued December 1, 1998), and application Serial No. 08/457,354 filed May 31, 1995 (now U.S. Patent No. 5,733,303, issued March 31, 1998). Application Serial No. 08/881,594 is a continuation of application Serial No. 782,467 filed January 10, 1997 (abandoned), which is a continuation of application Serial No. 08/457,354 filed May 31, 1995, which is a continuation of application Serial No. 08/282,181 filed July 28, 1994 (abandoned), which is a continuation-in-part of Application No. 08/213,272 filed March 17, 1994 which has issued as U.S. Patent No. 5,449,373. --;
Line 53, change "paralell" to -- parallel --;

Column 2,
Line 2, change "meander to" to -- meander --;
Line 40, change "illustration" to -- illustrations --;

Column 3,
Line 47, change "For to" to -- to --;

Column 4,
Line 11, change "pith" to -- with --;
Line 47, change "faith" to -- with --;

UNITED STATES PATENT AND TRADEMARK OFFICE
CERTIFICATE OF CORRECTION

PATENT NO. : 6,461,381 B2
DATED : October 8, 2002
INVENTOR(S) : Israel et al.

It is certified that error appears in the above-identified patent and that said Letters Patent is hereby corrected as shown below:

Column 5,
Line 13, insert -- ¶ The stent also includes...from each other --;

Column 6,
Line 2, insert -- ¶ In a preferred...upon its expansion --;
Line 10, delete "102, 103 and 104";
Line 11, change "As" to -- Thus, as --;
Lines 22 - 23, delete "¶ Rather the scope...which follow:";

Column 8,
Line 57, change "where in" to -- wherein --.

Signed and Sealed this

Tenth Day of June, 2003

JAMES E. ROGAN
*Director of the United States Patent and Trademark Office*